United States Patent [19]

Robbins

[11] 4,418,210

[45] Nov. 29, 1983

[54] PROCESS FOR PRODUCING ASYMMETRICAL THIOUREAS

[75] Inventor: Jeffrey D. Robbins, Berkeley, Calif.

[73] Assignee: Stauffer Chemical Company, Westport, Conn.

[21] Appl. No.: 334,705

[22] Filed: Dec. 28, 1981

[51] Int. Cl.³ .................................... C07C 157/05
[52] U.S. Cl. .................................................. 564/24
[58] Field of Search .................................... 564/24, 61

[56] References Cited

U.S. PATENT DOCUMENTS

| | | | |
|---|---|---|---|
| 1,477,804 | 12/1923 | Bedford et al. | 564/24 |
| 1,577,797 | 3/1926 | Flemming | 564/24 |
| 1,669,242 | 5/1928 | Heuser | 564/24 X |

FOREIGN PATENT DOCUMENTS 839797  6/1960  United Kingdom .................. 564/24

OTHER PUBLICATIONS

Schroeder, "Thioureas", *Chemical Reviews*, vol. 55, pp. 190–192 (1955).

*Primary Examiner*—Thomas A. Waltz
*Attorney, Agent, or Firm*—Michael J. Bradley

[57] ABSTRACT

A novel process for preparing asymmetrical thioureas having the formula

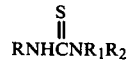

is disclosed, which comprises reacting $RNH_2$ with $CS_2$ in the presence of a base to produce $RNHCS_2^{\ominus}$ followed by reaction of the $RNHCS_2^{\ominus}$ with $R_1R_2NH$ in the presence of a catalytic amount of a base to produce the desired product.

3 Claims, No Drawings

PROCESS FOR PRODUCING ASYMMETRICAL THIOUREAS

BACKGROUND OF THE INVENTION

Asymmetrical thioureas, such as those described in U.S. Pat. No. 4,097,605 to Fancher, have required 2 or more reactions and isolation steps to produce. Fancher teaches the use of an intermediate isolated isothiocyanate which, when reacted with a properly selected amine, produces an asymmetrical thiourea.

Hodgkins et al., *J. Am. Chem. Soc.*, 83, 2532 (1961) teach the production and isolation of an isothiocyanate by reaction of an amine, $CS_2$ and base followed by reaction with ethyl chlorocarbonate. Takami et al., *Chem. Pharm. Bull.* (Japan), 21, 1311 (1973) teach the reversable formation of an isothiocyanate by the decomposition of a dithiocarbamic acid salt. None of these methods teach the production of asymmetrical thioureas.

BRIEF DESCRIPTION OF THE INVENTION

A process for forming asymmetrical thioureas in a single reaction vessel without intermediate isolation is disclosed herein. A thiourea having the formula $$\underset{\text{RNHCNR}_1\text{R}_2}{\overset{\text{S}}{\|}}$$

where R, $R_1$ and $R_2$ are as described below can be produced by reacting an amine having a formula $RNH_2$ and $CS_2$ in the presence of at least a molar equivalent of base, followed by addition of an amine having the formula $R_1R_2NH$ and excess base to the reaction mixture, and by further reaction to produce the desired product.

DETAILED DESCRIPTION OF THE INVENTION

Asymmetrical thioureas having the formula $$\underset{\text{RNHCNR}_1\text{R}_2}{\overset{\text{S}}{\|}}$$

wherein R is selected from the group of alkyl containing from 1 to 20 carbon atoms, preferably 4–12 carbon atoms, and most preferably 6–8 carbon atoms, cycloalkyl containing from 1 to 20 carbon atoms, preferably 4–12 carbon atoms, and most preferably 6–8 carbon atoms, and $R_1$ and $R_2$ are independently selected from the group consisting of hydrogen, alkyl containing from 1 to 20 carbon atoms, preferably 4–12 carbon atoms, and most preferably 6–8 carbon atoms, and cycloalkyl containing from 1 to 20 carbons, preferably 4–12 carbon atoms, most preferably 6–8 carbon atoms, provided that when $R_2$ is hydrogen, $R_1$ cannot equal R; comprising (1) forming a reaction mixture of water, an organic solvent, an amine having the formula $RNH_2$ (wherein R is as defined above), at least a molar equivalent of $CS_2$, and at least a molar equivalent of a base having the formula MOH wherein $M^\oplus$ is a cation, preferably $Na^\oplus$, that is selected from the group of $Na^\oplus$, $Li^\oplus$, $K^\oplus$, $Cs^\oplus$, or a quaternary ammonium ion having the formula $(R_3)_4N^\oplus$, wherein $R_3$ is a lower alkyl containing 1–4 carbon atoms;

(2) reacting said reaction mixture under suitable temperature and pressure conditions, preferably 0°–50° C. and 1 atmosphere pressure to form $RNHCS_2M$, wherein R is as stated above and $H_2O$;

(3) forming a second reaction mixture of comprising the mixture generated in step (2), an amine having the formula $R_1R_2NH$ wherein $R_1$ and $R_2$ are as described above and a catalytic amount of MOH, wherein M is as described above;

(4) reacting said second reaction mixture under suitable temperature and pressure conditions, preferably reflux temperature, to form said $$\underset{\text{RNHCHR}_1\text{R}_2}{\overset{\text{S}}{\|}} \text{ and MSH.}$$

In general, the reactions proceed as follows:

Reaction 1:

$$RNH_2 + MOH + CS_2 \longrightarrow RNHCS_2M + H_2O$$

Reaction 2:

$$RNHCS_2M + R_1R_2NH \xrightarrow[\text{of MOH}]{\text{catalytic amount}} \underset{\text{RNHCNR}_1\text{R}_2}{\overset{\text{S}}{\|}} + MSH$$

The $RNH_2$ and MOH are mixed with water and an inert organic solvent. $CS_2$ is added and the mixture stirred to form the dithiocarbamate salt. Some solvent is distilled off to remove excess $CS_2$. Then the $R_1R_2NH$ and excess MOH are added to the mixture, and the resulting mixture is heated until reaction is complete. The thiourea is isolated by separating the phases and stripping the organic phase.

The organic solvent utilized is preferably toluene but similar aromatic solvents or an alkane, cycloalkane, or any other water-immiscible organic solvent inert to the reaction conditions and possessing a convenient boiling point can be used.

The relative molar amounts of reactants for the two reactions are as follows:

Reaction 1:
  $RNH_2 = 1.0$
  $MOH = 1.0$ to 1.5, preferably 1.05 to 1.20
  $CS_2 = 1.0$ to 1.5, preferably 1.05 to 1.20

Reaction 2:
  $RNHCS_2M = 1.0$
  $R_1R_2NH = 1.0$ to 2.0, preferably 1.05 to 1.2
  $MOH = 0.05$ to 4.0, preferably 0.2 to 1.0 catalyst The reaction proceeds well at the reflux temperature of the reaction mixture but higher temperatures or longer reaction times appear to be necessary when smaller R groups are present. Increased pressures up to 3 atmospheres are useful to speed reaction times.

It is critical that the additional catalytic MOH be present in the second reaction to suppress rearrangement of the reactants with resultant formation of symmetrical thioureas.

The amount of water and organic solvent are not critical to the reaction; only sufficient amounts to solvate the reactants and provide good phase separation are required.

EXAMPLE I

N-(sec-heptyl)-N'-(n-octyl) thiourea

A round-bottom flask equipped with mechanical stirrer, dropping funnel, pH meter probe, thermometer, and nitrogen inlet was flushed with nitrogen and maintained under positive pressure of nitrogen. The flask was charged with 155 grams (g) (1.00 mole) of sec-heptylamine, 184 milliliters (ml) of water, 550 ml of toluene, and 84.0 g (1.05 mole) of 50% aqueous sodium hydroxide. A solution of 80 g (1.05 mole) of carbon disulfide in 50 ml of toluene was added over 0.2 hours with stirring, at 20°–21° C. Cooling was required. The pH was 12.8–13.1 throughout. After another fifty minutes of stirring, the apparatus was converted for distillation and 30 ml of distillate having a boiling point (b.p.) of 44°–46° C. at 104 Torr was taken. N-octylamine (130 g, 1.05 mole) and 16.0 g (0.200 mole) of 50% aqueous sodium hydroxide were added, the apparatus was converted for reflux, and the mixture was heated at reflux for 1.3 hours. Two hundred ml of water was added to the cooled mixture.

The mixture was phase separated and the aqueous phase extracted twice with 100 ml of toluene. The combined organics were washed with 100 ml of saturated brine, dried, and stripped at 50° C., 1 Torr for 1 hour, to give 280 g of a golden oil. Quantitative analysis of the oil by high performance liquid chromatography (hplc) showed that it contained 92.5 wt.% N-(sec-heptyl)-N'-(n-octyl) thiourea, about 2 wt.% N,N'-di(noctyl) thiourea, and less than 0.1 wt.% N,N'-di(sec-heptyl) thiourea. The yield of N-(sec-heptyl)-N'-(n-octyl) thiourea was 90.5%.

EXAMPLE II

N-(n-Butyl)-N'-(n-dodecyl) thiourea

An apparatus like the one described above was assembled, and the nitrogen-filled flask was charged with 15 g (0.20 mole) of n-butylamine, 17 ml of water, 16.8 g (0.21 mole) of 50% aqueous sodium hydroxide and 110 ml of toluene. A solution of 16 g (0.21 mole) of carbon disulfide in 10 ml of toluene was added, with stirring, over 0.1 hours at 0°–1° C. The pH increased from 13.6 to greater than 14 during the addition. After an additional 0.2 hour at 0° C., the reaction mixture was stirred for 0.5 hours at 20°–22° C. During this time the pH fell to 12.7. The apparatus was converted for distillation and 10 ml of distillate having a b.p. of 48° C. at 100 Torr was taken. To the residue was added 39 g (0.21 mole) of n-dodecylamine, 3.2 g (0.040 mole) of 50% aqueous sodium hydroxide, and 10 ml of toluene. The apparatus was converted for reflux and the mixture heated at reflux for 5.6 hours.

Saturated aqueous brine was added to the reaction mixture and the phases were separated while hot. The organic phase was dried and analyzed by thin layer chromotragraphy (tlc). The results of the analysis are discussed below. N-(n-butyl)-N'-(n-dodecyl) thiourea (m.p. 54°–59° C.) was isolated by recrystallization from toluene; it was seen by tlc analysis to be virtually free of the symmetrical thioureas. The technical yield of the crystalline product was 50%.

A similar preparation of N-(n-butyl)-N'-(n-dodecyl) thiourea had been carried out at an earlier time under similar conditions except that no catalytic NaOH had been added along with the n-dodecyl amine. Comparison of the tlc analysis of the earlier made product mixture with the tlc analysis of product mixture of Example II above showed that the latter contained a substantially higher proportion of the desired asymmetrical thiourea.

EXAMPLE III

Effect of added Sodium Hydroxide on the Extent of Formation of the Undesired Symmetrical Thioureas Sodium N-(sec-heptyl)dithiocarbamate in toluene and water was prepared as described above in Example I. After distillation of 30 ml of solvent as called for in Example I, the still warm mixture (36°–40° C.) was weighed and agitated to give a homogeneous-looking emulsion. No solid salt appeared to be present. The well-stirred emulsion was divided into three weighed portions. To portion number 1 was added 1.05 equivalents (i.e., 1.05 times the number of moles of sec-heptylamine used times the fraction of emulsion taken as portion number 1) of n-octylamine. To portion number 2 was added 1.05 equivalents of n-octylamine and 0.10 equivalents of 50% aqueous sodium hydroxide. To portion number 3 was added 1.05 equivalents of n-octylamine and 0.20 equivalents of 50% aqueous sodium hydroxide. Each mixture was heated at reflux for 1.3 hours, worked up as described in Example I and analyzed by hplc. The results are shown in the table.

TABLE

| Portion Number | Amount of NaOH Catalyst* | Technical Yield | Area % of the Thioureas (s-heptyl) di-(s-heptyl) | (n-octyl) | di-(n-octyl) |
|---|---|---|---|---|---|
| 1 | 0.05 equiv. | 98.7% | 7.5 | 86.4 | 6.1 |
| 2 | 0.15 equiv. | 99.5% | 1.4 | 96.5 | 2.1 |
| 3 | 0.25 equiv. | 98.5% | 0.6 | 98.0 | 1.4 |

*A 0.05 equivalent excess of NaOH is used in the preparation of the dithiocarbamate salt.

What is claimed is:

1. A process for preparing asymmetrical thioureas having the formula

$$\text{RNHCNR}_1\text{R}_2$$

wherein R and $R_1$ are independently selected from the group of alkyl containing from 1 to 20 carbon atoms and cycloalkyl containing from 1 to 20 carbon atoms, and $R_2$ is selected from the group consisting of hydrogen, alkyl containing from 1 to 20 carbon atoms and cycloalkyl containing from 1 to 20 carbon atoms and provided that when $R_2$ is hydrogen, $R_1$ can not equal R; comprising (1) forming a reaction of water, an organic solvent, an amine having the formula $RNH_2$, wherein R is as defined above, a molar excess of a base having the formula MOH wherein $M^{\oplus}$ is a cation selected from the group of $Na^{\oplus}$, $Li^{\oplus}$, $K^{\oplus}$, $Cs^{\oplus}$ and a quaternary ammonium ion having the formula $(R_3)_4N^{\oplus}$ wherein $R_3$ is a lower alkyl containing from 1 to 4 carbon atoms and $CS_2$;

(2) reacting said reaction mixture under suitable temperature and pressure conditions to form $RNHCS_2M$, wherein R is as defined above, and $H_2O$;

(3) forming a second reaction mixture comprising the mixture generated in step (2), an amine having the formula $R_1R_2NH$ wherein $R_1$ and $R_2$ are as described above and catalytic amount of MOH, wherein M is as described above; and
(4) reacting said second reaction mixture under suitable temperature and pressure conditions to form said
2. The process of claim 1 wherein R, $R_1$ and $R_2$ each contain from 4 to 12 carbon atoms.
3. The process of claim 1 wherein R, $R_1$ and $R_2$ each contain from 6-8 carbon atoms.
* * * * *

UNITED STATES PATENT AND TRADEMARK OFFICE
CERTIFICATE OF CORRECTION

PATENT NO. :   4,418,210

DATED      :   November 29, 1983

INVENTOR(S) :  Jeffrey D. Robbins

It is certified that error appears in the above-identified patent and that said Letters Patent is hereby corrected as shown below:

In column 4, at line 54, after the word "reaction" please insert the following --- mixture ---.

Signed and Sealed this

Sixth Day of November 1984

[SEAL]

Attest:

Attesting Officer

GERALD J. MOSSINGHOFF

Commissioner of Patents and Trademarks